(12) United States Patent
Cox

(10) Patent No.: US 9,408,877 B1
(45) Date of Patent: Aug. 9, 2016

(54) COMPOSITIONS AND PROCESS FOR SKIN RESTORATION

(71) Applicant: Marcia Patricia Cox, Whippany, NJ (US)

(72) Inventor: Marcia Patricia Cox, Whippany, NJ (US)

(*) Notice: Subject to any disclaimer, the term of this patent is extended or adjusted under 35 U.S.C. 154(b) by 742 days.

(21) Appl. No.: 13/861,458

(22) Filed: Apr. 12, 2013

(51) Int. Cl.
| | | |
|---|---|---|
| *A01N 65/00* | (2009.01) | |
| *A61K 35/60* | (2006.01) | |
| *A61K 36/534* | (2006.01) | |
| *A61K 36/63* | (2006.01) | |
| *A61K 36/752* | (2006.01) | |
| *A61K 45/06* | (2006.01) | |

(52) U.S. Cl.
CPC ............ *A61K 35/60* (2013.01); *A61K 36/534* (2013.01); *A61K 36/63* (2013.01); *A61K 36/752* (2013.01); *A61K 45/06* (2013.01)

(58) Field of Classification Search
CPC .................................................. A61K 36/00
USPC ........................................................ 424/725
See application file for complete search history.

(56) References Cited

U.S. PATENT DOCUMENTS

| | | |
|---|---|---|
| 5,972,322 A | 10/1999 | Rath et al. |
| 6,280,751 B1 | 8/2001 | Fletcher et al. |
| 7,348,034 B2 | 3/2008 | Murray et al. |
| 8,147,854 B2 | 4/2012 | Okawa et al. |
| 2007/0020213 A1 | 1/2007 | Tamarkin et al. |
| 2007/0196325 A1 | 8/2007 | Zhang et al. |
| 2007/0286876 A1 | 12/2007 | Warren et al. |
| 2008/0260655 A1 | 10/2008 | Tamarkin et al. |
| 2009/0149361 A1 | 6/2009 | Adkison et al. |
| 2009/0324506 A1 | 12/2009 | Seidling et al. |

*Primary Examiner* — Michael Meller
(74) *Attorney, Agent, or Firm* — Irving M. Fishman

(57) ABSTRACT

A skin restoration cream formulated to treat and soothe skin conditions such as dandruff, psoriasis, eczema, cold sores, and other conditions. The skin restoration cream has natural and essential oils, which are free of artificial fragrances, steroids and other chemicals that may cause unwanted side effects. The composition is a healthy option for treating a variety of skin conditions or disorders. An embodiment of the composition formulates a muscle therapy treatment to alleviate and soothe muscle pain.

26 Claims, No Drawings

COMPOSITIONS AND PROCESS FOR SKIN RESTORATION

BACKGROUND OF THE INVENTION

Embodiments of the present invention generally relate to compositions and processes for making a skin restoration cream for alleviating skin irritation conditions.

Skin irritation conditions such as dandruff are problems that humans are constantly struggling to alleviate. Particularly when untreated, these conditions worsen over time, and there are many medications and shampoos for treating dandruff that include chemicals. One of the problems of the users of dandruff controlling compositions is the development of allergic reactions. These allergic reactions can be caused by the fragrances present in shampoos and scalp products. Further, the allergic reactions can develop over time in fragrances that are ubiquitously present in most commercial shampoos, hair, and scalp products. Even when these products are used quickly and rinsed out thoroughly the allergic symptoms persist in some consumers.

Additionally steroid treatments are also being used to treat the scalp conditions, and these also have limited applications due to possible side effects. Thus, these are not desired by consumers. Consumers prefer to avoid using strong synthetic chemicals and desire natural products based solutions in the formulation of creams and shampoos.

Efforts to incorporate vitamins that are described in the literature as nutrients for hair growth have been met with limited success by the inventor, especially vitamin A and vitamin D in the form of vitamin A&D ointment. Addition of minerals such as zinc oxide mixed in with Vitamin A&D ointment did not affect any changes in the allergic symptoms and dandruff flakes. Further, covering the scalp areas with petroleum jelly did result in moist flakes on the scalp.

Given the above, it would be advantageous to have a skin care composition which does not irritate the scalp and contains natural ingredients.

BRIEF SUMMARY OF THE INVENTION

Briefly stated, in one aspect of the present invention, a skin restoration composition is provided. The skin restoration composition includes an essential oil, natural oils, fish oil and a carrier, wherein the essential oil comprises peppermint oil and wherein the skin restoration composition when applied to a scalp of a subject prevents dandruff and flaking of the scalp.

In another aspect of the present invention, a method for preparing a skin restoration composition is provided. This method includes: providing a skin restoration composition including an essential oil, natural oils, fish oil and a carrier, wherein the essential oil comprises peppermint oil; and mixing the components of the skin restoration composition.

In yet another aspect of the invention, a method of restoring skin is provided. This method includes applying the skin restoration cream including an essential oil, natural oils, fish oil and a carrier, wherein the essential oil comprises peppermint oil to a person subject to dandruff.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Disclosed herein is a skin restoration composition, comprising natural oils, an essential oil, fish oil and a carrier. The essential oil comprises peppermint oil and the skin restoration composition when applied to the scalp of a subject prevents dandruff and flaking of the scalp. Disclosed herein is a method for preparing a skin restoration composition by mixing the above mentioned ingredients. Also disclosed is a method of alleviating skin irritation in the scalp of a person by applying the skin restoration composition thereto. An embodiment of the composition comprises peppermint oil, cod-liver oil, olive oil and petrolatum.

Skin restoration cream referred to herein is a heterogeneous mixture of natural oils, an essential oil, vitamins and other ingredients. Components of the skin restoration composition are described herein.

The compositions as referred to herein are referred to as percentage of the total composition including the carrier.

The carrier of the skin restoration cream as referred to herein include petroleum jelly.

The carrier of the skin restoration cream as referred to herein includes a carbomer. The carbomer can be used to dilute the petroleum jelly to obtain the desired application viscosity of the skin restoration cream. In one embodiment, the quantity of petroleum jelly present in the cream can be reduced to approximately one-third (⅓) when including the carbomer. Typically, carbomer 940 can be used, and in embodiments in which the petroleum jelly is reduced to approximately one-third (⅓), the skin composition can include water and sodium bicarbonate. In one embodiment, approximately one-half (½) teaspoon of sodium bicarbonate and one (1) tablespoon of carbomer 940 were utilized for each four (4) ounces of water. This embodiment also operates as a hair styling lotion that eliminates, or minimizes, dandruff and scales on the scalp. Another advantage is that this hair styling lotion can be used for a wider variety of hair types due to the lower oiliness of this lotion.

The terms skin restoration cream and skin restoration composition have the same active ingredients such as natural oils, essential oils, fish oil and the carrier as referred to herein.

The skin restoration cream as referred to herein can be used in muscle therapy. Application of the cream alleviates or soothes muscle pain, and the stronger strength formulation is preferred for such applications.

As referred to herein, flaking means detachment of pieces of the skin formed on the scalp.

As referred to herein, skin irritation include raw patches, scabs, redness and other skin conditions that are associated with unhealthy skin conditions.

EXAMPLE 1

A female user had symptoms of dandruff and psoriasis for over twenty years. Countless treatments were used without long term success. After using the skin restoration cream of the present invention, the flaking, redness, and peeling of the scalp not only diminished, but completely cleared. With continued use over an eleven month period, the scalp continued a healthy state. The skin restoration cream also cleared psoriasis on the face and neck, and restored irritated skin on other areas of the body when used regularly.

EXAMPLE 2

A female user found the skin restoration cream of the present invention effective for itchy, scaly scalp as well as for eczema and rash. Eczema and rashes were previously treated with steroid creams provided by physicians or over the counter. The eczema and rash seemed to return as soon as the user stopped using the steroid cream. After using the skin restoration cream of the present invention, results were immediate. The user weaned off the steroid cream. During the seven months of use, the user's skin remained clear and soft.

Essential Oils

Essential oils as described herein are concentrated hydrophobic liquids containing volatile aroma compounds from plants. These are also known as volatile oils, ethereal oils or aetherolea and are generally extracted by distillation and other processes including solvent extraction and genetic expression. A feature of essential oils is that it carries a distinctive scent, or essence, of the plant. Generally essentials oils are used in various applications; however, there are no distinctive categories for any medical, pharmacological, or culinary purpose. For example, they are widely used in perfumes, cosmetics, soaps, shampoos, household cleaning products, and for flavoring food and drink. Medical applications for essential oils include treatment of cancer and these are subject to regulation in most countries. Essential oils as referred to herein include lavender oil, rosemary oil, sandalwood oil, geranium oil, thyme oil, sage oil, cedar-wood oil, basil oil, cypress oil and peppermint oil. Preferred essential oils are selected from peppermint oil, spearmint oil, sandalwood oil, lavender oil, and the most preferred is peppermint oil. According to an in vitro report by The Longwood Herbal Task Force, " . . . Peppermint and menthol have significant antiviral activity and moderate antibacterial activity against both Gram-positive and Gram-negative bacteria and are fungicidal against *Candida albicans, Aspergillus albus* and other fungi." http://www.longwoodherbal.org/peppermint/peppermint.cis.PDF. The preferred range of essential oil (e.g., peppermint oil) in the skin restoration cream ranges from 0.25 wt % to 50% wt % based on the weight of the total composition. The most preferred range of essential oil (e.g., peppermint oil ranges) from 0.25 wt % to 25 wt %.

Fish Oil

Fish oil as described herein is derived from the tissues of oily fish and contains the omega-3 fatty acids, eicosapentaenoic acid ("EPA") and docosahexaenoic acid ("DHA"). The benefit of using fish oil is that these precursors benefit in curing cancer. Other oily fish, such as tuna, also contain omega-3 in somewhat lesser amounts. Diets supplemented with cod liver oil have shown beneficial effects on psoriasis. See Wolters, M. (2005). "Diet and psoriasis: experimental data and clinical evidence"; *British Journal of Dermatology* 153 (4): 706-14. The preferred range of fish oil (e.g., cod liver oil) in the skin restoration cream ranges from 0.25 wt % to 50% wt % based on the weight of the total composition. The most preferred range of fish oil (e.g., cod liver oil) ranges from 0.25 wt % to 25 wt %.

Natural Oils

Natural oil acts as a carrier for the essential oil and fish oil in the skin restoration cream. The danger of applying an essential oil is generally dependant on its purity grade because many essential oils are designed exclusively for their aroma-therapeutic quality. Generally these essential oils should not be applied directly to the skin in their net or undiluted form because conditions such as severe irritation and allergic reaction over time can develop into hepatotoxicity. Consequently, non-therapeutic grade essential oils are not recommended for topical or internal use. Additionally, essential oils should not be used with animals, as they possess extreme hepatotoxicity and dermal toxicity for animals, especially for cats. Therefore, essential oils are blended with natural oil before being applied to the skin of a person. Carrier oil as defined herein is an oil obtained by cold pressing the edible seeds or fruits of a plant. Examples of carrier oil are olive oil, jojoba oil, coconut oil, castor oil and avocado oil. Common carrier oils include olive oil, almond oil, hazelnut oil and grape seed oil. Particularly, extra virgin olive oil that has been cold pressed from freshly harvested olives and does not contain chemicals is preferred. Olive oil strengthens and smoothen hair cuticles. Additionally, is believed to help in preventing as well as curing hair loss as it prevents the production of the hormone DTH. DTH hormone causes the hair follicle shaft to decrease and regular application of olive oil helps in the problem of hair loss. Further, for relaxed/permed hair in females, excessive chemical use can cause hair damage and use of olive oil that contains antioxidants can promote healthy hair and scalp. The preferred range of natural oil (e.g., olive oil) in the skin restoration cream ranges form from 0.25 wt % to 50% wt % based on the weight of the total composition. The most preferred range of natural oil (e.g., olive oil) ranges from 0.25 wt % to 25 wt %.

Citrus Peel Oil

Citrus peel oils are additional natural oils that are derived from cold pressing of the peel of the citrus species. Citrus peel oils are used in the present composition for providing scent and to mask the odor of fish oils. Examples of citrus oils are lemon, lime, orange, and tangerine. Preferred citrus peel oil is lemon oil. The preferred range of lemon oil in the skin restoration cream ranges from 0.25 wt % to 50 wt % based on the weight of the total composition. The most preferred range of lemon oil ranges from 0.25 wt % to 40 wt %.

Petroleum Waxes

The carrier for the skin restoration composition can include petroleum waxes such as white petroleum jelly, also known as petrolatum or vaseline. White petroleum jelly provides body to the present skin restoration cream, and the overall viscosity should be about 600 to about 6000 cps. The preferred range of petroleum waxes (e.g., petroleum jelly) in the skin restoration cream ranges from 0.25 wt % to 95 wt % based on the weight of the total composition. The most preferred range of petroleum waxes (e.g., petroleum jelly) ranges from 0.25 wt % to 90 wt %.

Dandruff

Dandruff is a common scalp disorder affecting many humans and dandruff is referred to in latin as Pityriasis simplex capillitii. Dandruff is the defoliation of dead skin cells from the scalp of a person and is not to be confused with a simple dry scalp. Usually, as skin cells die, a small amount of flaking of the skin occurs and about 487,000 cells/cm$^2$ of the scalp get released normally after detergent treatment. See *"Dandruff: The most commercially exploited skin disease"*, *Indian J Dermatol* 55 (2): 130-134. Unusually large amounts of flaking can occur chronically and up to 800,000 cells/cm$^2$ of the scalp which can be accompanied by redness and irritation of the scalp. Dandruff often causes itching, and keratinocytes play a key role in the expression and generation of immunological reactions during dandruff formation. As the epidermal layer continually replaces itself, cells are pushed outward where they eventually die and flake off. The skin of the scalp protects the head and the follicular density is much higher, creating a dark, warm and moist environment. This provides thermal insulation, but also is conducive to parasitic infestation. Particularly, scalp specific fungus, *Malassezia globosa* metabolizes triglycerides present in sebum and results in a lipid byproduct oleic acid ("OA") that is believed to cause dandruff. Penetration by OA of the top layer of the epidermis, the stratum corneum, results in an inflammatory response in susceptible persons which disturbs homeostasis and results in erratic cleavage of stratum corneum cells. See, Dawson T L (2006). "*Malassezia* and seborrheic dermatitis: etiology and treatment". *Journal of cosmetic science* 57 (2): 181-2. Additionally, when the scalp skin is subjected to brushing, it can cause friction and introduce microorganisms. Dandruff can also be caused by an allergic reaction to chemicals in hair gels, sprays, and shampoos, or sometimes even dandruff medications.

Psoriasis

Psoriasis is a chronic, relapsing inflammatory disease that occurs in a few percent of the population and mostly involves their scalp area. See, Sinclair, R, Banfield, C, Dawber, R, (eds). Infections and infestations of the hair. In: Handbook of Diseases of the Hair and Scalp. Malden, M A: Blackwell Science, p 191-200, 1999. Friction injury in the scalp and lack of UV exposure may cause psoriasis. Psoriasis is plaques covered by a silver-gray scale appearing at the hair margins as well as on hair-bearing areas. These plaques appear similar to dandruff and with the progression of disease scalp lesions may be similar to those found in seborrheic dermatitis. Scalp psoriasis can be very difficult to treat, and most mild cases of scalp psoriasis are treated with tar shampoo. Also, salicylic acid may be used to break down scales, and topical corticosteroids may also be used to treat this disease. In severe cases, or those associated with significant hair loss, treatment may require systemic anti-psoriatic therapy such as methotrexate or cyclosporine.

In treating a flaky scalp, initial flakes must be removed during the application of shampoo so as to ensure that the skin restoration cream is applied to a thoroughly cleaned scalp. Care must be taken to rub the skin restoration cream over the entire scalp area. If an area is missed, then flakes may appear in those areas. When ingredients to soothe the skin such as menthol are used in the skin restoration composition, lower amounts of compositional ingredients such as essential oil, fish oil may be effective in alleviating dandruff. This is particularly useful when the sensation of applying menthol persists for a longer time. As the skin restoration cream is oil based, its oils may help hair to look healthier. As the ingredients are all natural and the fragrance from the lemon oil is pleasant, no allergic reaction may be observed.

In an embodiment, the skin restoration composition may be used on the face and the blemishes and dark spots being reduced with the pores on the skin being clearly visible. Care must be taken to avoid the skin restoration cream on sensitive areas such as eyes. In a typical application on the face and neck can be done at night before sleeping. Advantages of applying the skin restoration cream on areas such as forehead and eyebrows is that overproduction of dead skin and patchy flakes are minimized. Additional uses of the skin restoration cream include, but are not limited to, treating minor acne present on the face and buttocks and soothing inflamed skin caused by allergic reaction to dust mites, brastraps, and/or nickel. In another embodiment, soothing of the aching muscles in fibromyalgia sore spots can be obtained by using higher levels of essential oil and/or cod-liver oil in the skin restoration cream.

The present invention is further described by the example which follows. Such examples, however, are not to be construed as limiting in any way either the spirit or the scope of the present invention.

TABLE 1

Muscle Therapy Embodiment

|  | Low Strength | | Medium Strength | | High Strength | |
| --- | --- | --- | --- | --- | --- | --- |
|  | min | max | min | max | min | max |
| Lemon Oil | 11.00% | 20.00% | 20.00% | 20.00% | 20.00% | 20.00% |
| Peppermint Oil | 10.00% | 19.99% | 20.00% | 39.99% | 40.00% | 60.00% |
| Petroleum Jelly | 79.00% | 60.01% | 60.00% | 40.01% | 40.00% | 20.00% |
|  | 100.00% | 100.00% | 100.00% | 100.00% | 100.00% | 100.00% |

TABLE 2

Skin Restoration Cream

Regular Strength

| Ingredient | Tsp | Ratio | % 3 sig fig | % 2 sig fig | |
| --- | --- | --- | --- | --- | --- |
| Lemon Oil | 2 | 0.021621622 | 2.16 | 2.2 | 2.2% |
| Peppermint Oil | 1.5 | 0.016216216 | 1.62 | 1.6 | 1.6% |
| Olive Oil | 5 | 0.054054054 | 5.41 | 5.4 | 5.4% |
| Cod Liver Oil | 6 | 0.064864865 | 6.49 | 6.5 | 6.5% |
| Petroleum Jelly | 78 | 0.843243243 | 84.32 | 84.3 | 84.3% |
| Total | 92.5 | 1 | 100 | 100 | 100.0% |

Maximum Strength

| Ingredient | Tsp | Ratio | % 3 sig fig | % 2 sig fig | |
| --- | --- | --- | --- | --- | --- |
| Lemon Oil | 2 | 0.03539823 | 3.54 | 3.5 | 3.5% |
| Peppermint Oil | 1.5 | 0.026548673 | 2.65 | 2.7 | 2.7% |
| Olive Oil | 5 | 0.088495575 | 8.85 | 8.8 | 8.8% |
| Cod Liver Oil | 6 | 0.10619469 | 10.62 | 10.6 | 10.6% |
| Petroleum Jelly | 42 | 0.743362832 | 74.34 | 74.3 | 74.3% |
| Total | 56.5 | 1 | 100.00 | 100.0 | 100.0% |

Minimum Strength

| Ingredient | Tsp | Ratio | % 3 sig fig | % 2 sig fig | |
| --- | --- | --- | --- | --- | --- |
| Lemon Oil | 2 | 0.010958904 | 1.10 | 1.1 | 1.1% |
| Peppermint Oil | 1.5 | 0.008219178 | 0.82 | 0.8 | 0.8% |
| Olive Oil | 5 | 0.02739726 | 2.74 | 2.7 | 2.7% |
| Cod Liver Oil | 6 | 0.032876712 | 3.29 | 3.3 | 3.3% |
| Petroleum Jelly | 168 | 0.920547945 | 92.05 | 92.1 | 92.1% |
| Total | 182.5 | 1 | 100.00 | 100.0 | 100.0% |

|  | Lowest | Highest | Tolerance |
| --- | --- | --- | --- |
| Lemon Oil | 1.10% | 3.50% | 0.54% |
| Peppermint Oil | 0.80% | 2.70% | |
| Olive Oil | 2.70% | 8.80% | |
| Cod Liver Oil | 3.30% | 10.60% | |
| Petroleum Jelly | 92.10% | 74.30% | |
|  | 100.00% | 100.00% | |

Other Ingredients

| Cod Liver oil (per tsp): | IU |
| --- | --- |
| Vitamin A (retinyl Palmitate) | 5000 |
| Vitamin $D^3$ (cholecalciferol) | 38 |
| Vitamin E (d-alpha tocopheryl acetate) | 5 |

TABLE 2-continued

Skin Restoration Cream

| | |
|---|---|
| Total Omega-3 fatty acids: | 1081 mg |
| DHA (docosahexaenoic acid) | 460 mg |
| EPA (eicosapentaenoic acid) | 345 mg |
| Other Omega-3's | 276 mg |
| Natural lemon flavor | |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A composition for muscle therapy or for the treatment of a skin condition selected from the group consisting of skin irritation, dandruff, flaking of the scalp, eczema, psoriasis and acne
consisting essentially of:
0.25-25% of cod liver oil,
0.5-25% of peppermint oil,
0.5-50% of citrus peel oil,
0.5-50% of a natural oil selected from the group consisting of olive oil, jojoba oil, coconut oil, castor oil, avocado oil, almond oil, hazelnut oil, and grape seed oil, and
0.25-95% of petroleum jelly.

2. The composition of claim 1 wherein said natural oil is olive oil.

3. The composition of claim 1 wherein the citrus peel oil is selected from the group consisting of lemon oil, lime oil, orange oil, and tangerine oil.

4. The composition of claim 1 wherein the citrus peel oil is lemon oil.

5. The composition of claim 1 wherein:
said cod liver oil is present in an amount of 3.3 to 10.6%,
said peppermint oil is present in an amount of 0.8-2.7%,
said citrus peel oil is present in an amount of 1.1-3.5%,
said natural oil is present in an amount of 2.7-8.8%, and
said petroleum jelly is present in an amount of 74.3-92.1%.

6. The composition of claim 5 wherein
said cod liver oil is present in an amount of 3.3%,
said peppermint oil is present in an amount of 0.8%,
said citrus peel oil is present in an amount of 1.1%,
said natural oil is present in an amount of 2.7%, and
said petroleum jelly is present in an amount of 92.1%.

7. The composition of claim 5 wherein
said cod liver oil is present in an amount of 6.5%,
said peppermint oil is present in an amount of 1.6%,
said citrus peel oil is present in an amount of 2.2%,
said natural oil is present in an amount of 5.4%, and
said petroleum jelly is present in an amount of 84.3%.

8. The composition of claim 5 wherein
said cod liver oil is present in an amount of 10.6%,
said peppermint oil is present in an amount of 2.7%,
said citrus peel oil is present in an amount of 3.5%,
said natural oil is present in an amount of 8.8%, and
said petroleum jelly is present in an amount of 74.3%.

9. A composition for muscle therapy or for the treatment of a skin condition selected from the group consisting of skin irritation, dandruff flaking of the scalp, eczema, psoriasis and acne
consisting essentially of:
0.25-25% of cod liver oil,
0.5-25% of peppermint oil,
0.5-25% of an essential oil selected from the group consisting of lavender oil, rosemary oil, sandalwood oil, geranium oil, thyme oil, sage oil, cedar-wood oil, basil oil, cypress oil, and spearmint oil,
0.5-50% of citrus peel oil,
0.5-50% of a natural oil selected from the group consisting of olive oil, jojoba oil, coconut oil, castor oil, avocado oil, almond oil, hazelnut oil, and grape seed oil, and
0.25-95% of petroleum jelly;
wherein the combined amount of the peppermint oil and the essential oil is no more than 25%.

10. The composition of claim 9 wherein said natural oil is olive oil.

11. The composition of claim 9 wherein the citrus peel oil is selected from the group consisting of lemon oil, time oil, orange oil, and tangerine oil.

12. The composition of claim 9 wherein the citrus peel oil is lemon oil.

13. The composition of claim 9 wherein
said cod liver oil is present in an amount of 3.3-10.6%,
said peppermint oil is present in an amount of 0.8-2.7%,
said essential oil is present in an amount of 0.5-2.7%,
said citrus peel oil is present in an amount of 1.1-3.5%,
said natural oil is present in an amount of 2.7-8.8%, and
said petroleum jelly is present in an amount of 74.3-92.1%;
wherein the combined amount of essential oil and peppermint is not more than 2.7%.

14. The composition of claim 13, wherein
said cod liver oil is present in an amount of 3.3%,
said peppermint oil is present in an amount of 0.8%,
said essential oil is present in an amount of 0.5%,
said citrus peel oil is present in an amount of 1.1%,
said natural oil is present in an amount of 2.7%, and
said petroleum jelly is added in to form the remainder of the composition.

15. The composition of claim 13, wherein
said cod liver oil is present in an amount of 6.5%,
said peppermint oil is present in an amount of 0.8-1.6%,
said essential oil is present in an amount of 0.5-1.6%,
said citrus peel oil is present in an amount of 2.2%,
said natural oil is present in an amount of 5.4%, and
said petroleum jelly is present in an amount of 84.3%;
wherein the combined amount of essential oil and peppermint oil is not more than 1.6%.

16. The composition of claim 13, wherein
said cod liver oil is present in an amount of 10.6%,
said peppermint oil is present in an amount of 0.8-2.7%,
said essential oil is present in an amount of 0.5-2.7%,
said citrus peel oil is present in an amount of 3.5%,
said natural oil is present in an amount of 8.8%, and
said petroleum jelly is present in an amount of 74.3%;
wherein the combined amount of essential oil and peppermint oil is not more than 2.7%.

17. A composition for muscle therapy or for the treatment of a skin condition selected from the group consisting of skin irritation, dandruff, flaking of the scalp, eczema, psoriasis and acne
consisting of:
0.25-25% of cod liver oil,
0.5-25% of peppermint oil,
0.5-50% of citrus peel oil,
0.5-50% of a natural oil selected from the group consisting of olive oil, jojoba oil, coconut oil, castor oil, avocado oil, almond oil, hazelnut oil, and grape seed oil, and
0.25-95% of petroleum jelly.

18. The composition of claim 17 wherein
said cod liver oil is present in an amount of 33 to 10.6%, said peppermint oil is present in an amount of 0.8-2.7%,
said citrus peel oil is present in an amount of 1.1-3.5%,
said natural oil is present in an amount of 2.7-8.8%, and
said petroleum jelly is present in an amount of 74.3-92.1%.

19. The composition of claim 18 wherein
said cod liver oil is present in an amount of 3.3%,
said peppermint oil is present in an amount of 0.8%,
said citrus peel oil is present in an amount of 1.1%,
said natural oil is olive oil and is present in an amount of 2.7%, and
said petroleum jelly is present in an amount of 92.1%.

20. The composition of claim 18 wherein
said cod liver oil is present in an amount of 6.5%,
said peppermint oil is present in an amount of 1.8%,
said citrus peel oil is present in an amount of 2.2%,
said natural oil is olive oil and is present in an amount of 5.4%, and
said petroleum jelly is present in an amount of 84.3%.

21. The composition of claim 18 wherein
said cod liver oil is present in an amount of 10.6%,
said peppermint oil is present in an amount of 2.7%,
said citrus peel oil is present in an amount of 3.5%,
said natural oil is olive oil and is present in an amount of 8.8%, and
said petroleum jelly is present in an amount of 74.3%.

22. A composition for muscle therapy or for the treatment of a skin condition selected from the group consisting of skin irritation, dandruff, flaking of the scalp, eczema, psoriasis and acne
consisting of:
0.25-25% of cod liver oil,
0.5-25% of peppermint oil,
0.5-25% of an essential oil selected from the group consisting of lavender oil, rosemary oil, sandalwood oil, geranium oil, thyme oil, sage oil, cedar-wood oil, basil oil, cypress oil, and spearmint oil,
0.5-50% of citrus peel oil,
0.5-50% of a natural oil selected from the group consisting of olive oil, jojoba oil, coconut oil, castor oil, avocado oil, almond oil, hazelnut oil, and grape seed oil, and
0.25-95% of petroleum jelly,
wherein the combined amount of peppermint oil and the essential oil is not more than 25%.

23. The composition of claim 22 wherein
said cod liver oil is present in an amount of 3.3 to 10.6%,
said peppermint oil is present in an amount of at least 0.8%,
said essential oil is present in amount of at least 0.5%,
said citrus peel oil is present in an amount of 1.1-3.5%,
said natural oil is present in an amount of 2.7-8.8%, and
said petroleum jelly is present in an amount of 74.3-92.1%;
wherein the combined amount of essential oil and peppermint oil is not more than 2.7%.

24. The composition of claim 23, wherein
said cod liver oil is present in an amount of 3.3%,
said peppermint oil is present in an amount of 0.8%,
said essential oil is present in an amount of 0.5%,
said citrus peel oil is present in an amount of 1.1%,
said natural oil is present in an amount of 2.7%, and
said petroleum jelly is added in to form the remainder of the composition.

25. The composition of claim 23, wherein
said cod liver oil is present in an amount of 6.5%,
said peppermint oil is present in an amount of 0.8-1.6%,
said essential oil is present in an amount of 0.5-1.6%,
said citrus peel oil is present in an amount of 2.2%,
said natural oil is present in an amount of 5.4%, and
said petroleum jelly is present in an amount of 84.3%;
wherein the combined amount of essential oil and peppermint oil is not more than 1.6%.

26. The composition of claim 23, wherein
said cod liver oil is present in an amount of 10.6%,
said peppermint oil is present in an amount of 0.8-2.7%,
said essential oil is present in an amount of 0.5-2.7%,
said citrus peel oil is present in an amount of 3.5%,
said natural oil is present in an amount of 8.8%, and
said petroleum jelly is present in an amount of 74.3%;
wherein the combined amount of essential oil and peppermint oil is not more than 2.7%.

\* \* \* \* \*